United States Patent
Eidenschink et al.

(10) Patent No.: US 7,306,616 B2
(45) Date of Patent: Dec. 11, 2007

(54) BALLOON CATHETER AND METHOD OF MAKING SAME

(75) Inventors: Tracee Eidenschink, Wayzata, MN (US); Brett A. Williams, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 598 days.

(21) Appl. No.: 10/431,231

(22) Filed: May 5, 2003

(65) Prior Publication Data

US 2004/0225318 A1    Nov. 11, 2004

(51) Int. Cl.
*A61M 29/00* (2006.01)
*A61M 35/00* (2006.01)

(52) U.S. Cl. .................... 606/194; 604/103.08

(58) Field of Classification Search ........ 606/191–194; 604/103–104, 264; 600/207; 128/898
See application file for complete search history.

(56) References Cited

U.S. PATENT DOCUMENTS

| | | | |
|---|---|---|---|
| 4,002,709 A | 1/1977 | Mozer | 264/90 |
| 4,490,421 A | 12/1984 | Levy | 428/35 |
| RE32,983 E | 7/1989 | Levy | 428/36.92 |
| 4,906,241 A | 3/1990 | Noddin et al. | 606/194 |
| 4,906,244 A | 3/1990 | Pinchuk et al. | 606/194 |
| 4,952,357 A | 8/1990 | Euteneuer | 264/129 |
| 4,963,133 A | 10/1990 | Whipple | 604/283 |
| RE33,561 E | 3/1991 | Levy | 428/36.92 |
| 5,041,125 A | 8/1991 | Montano, Jr. | 606/192 |
| 5,087,394 A | 2/1992 | Keith | 204/22 |
| 5,108,415 A | 4/1992 | Pinchuk et al. | 606/194 |
| 5,156,612 A | 10/1992 | Pinchuk et al. | 606/194 |
| 5,250,070 A | 10/1993 | Parodi | 606/194 |
| 5,264,260 A | 11/1993 | Saab | 428/35.5 |
| 5,304,340 A | 4/1994 | Downey | 264/521 |
| 5,318,587 A * | 6/1994 | Davey | 606/194 |
| 5,411,477 A | 5/1995 | Saab | 604/96 |
| 5,496,276 A | 3/1996 | Wang et al. | 604/96 |
| 5,500,181 A | 3/1996 | Wang et al. | 264/532 |
| 5,545,132 A * | 8/1996 | Fagan et al. | 604/103.08 |
| 5,714,110 A | 2/1998 | Wang et al. | 264/529 |
| 5,733,301 A | 3/1998 | Forman | 606/192 |
| 5,807,520 A | 9/1998 | Wang et al. | 264/520 |
| 5,826,588 A * | 10/1998 | Forman | 128/898 |
| 5,948,345 A | 9/1999 | Patel et al. | 264/529 |
| 6,013,055 A | 1/2000 | Bampos et al. | 604/96 |
| 6,110,192 A * | 8/2000 | Ravenscroft et al. | 606/194 |
| 6,193,738 B1 | 2/2001 | Tomaschko et al. | 606/194 |
| 6,228,072 B1 | 5/2001 | Omaleki et al. | 604/529 |
| 6,287,506 B1 | 9/2001 | Hudgins et al. | 264/515 |
| 6,328,710 B1 | 12/2001 | Wang et al. | 604/96.01 |
| 6,458,313 B2 | 10/2002 | Hudgins et al. | 264/515 |

(Continued)

FOREIGN PATENT DOCUMENTS

EP    0 318 919    1/1994

(Continued)

*Primary Examiner*—Anhtuan T. Nguyen
*Assistant Examiner*—Amanda Adams
(74) *Attorney, Agent, or Firm*—Vidas, Arrett, Steinkraus (57) ABSTRACT

A balloon catheter method of providing same, wherein a balloon catheter defines one or more indentations which provide improved flexibility to at least a portion of the catheter shaft and/or improved folding and rewrapping characteristics to the balloon.

19 Claims, 9 Drawing Sheets

U.S. PATENT DOCUMENTS

| | | |
|---|---|---|
| 6,488,654 B2 | 12/2002 | Gonzalez et al. ...... 604/103.06 |
| 6,491,711 B1 * | 12/2002 | Durcan ...................... 606/194 |
| 6,544,224 B1 | 4/2003 | Steese-Bradley ....... 604/103.06 |
| 7,083,639 B2 * | 8/2006 | Guinan et al. ................ 623/1.1 |
| 2001/0011178 A1 | 8/2001 | Tomaschko et al. ........ 606/192 |
| 2001/0016705 A1 | 8/2001 | Omaleki et al. ....... 604/103.06 |
| 2001/0027310 A1 | 10/2001 | Parisi et al. ................. 604/524 |
| 2002/0072707 A1 | 6/2002 | Gonzalez et al. ...... 604/103.06 |
| 2002/0110657 A1 | 8/2002 | Wang et al. ............... 428/35.7 |
| 2003/0078613 A1 | 4/2003 | Heidner ...................... 606/194 |

FOREIGN PATENT DOCUMENTS

| | | |
|---|---|---|
| EP | 0 485 903 | 10/1996 |
| EP | 0 783 897 A2 | 7/1997 |
| EP | 0 783 897 A3 | 8/1999 |
| EP | 1 316 326 A1 | 6/2003 |
| EP | 1625869 | 2/2006 |
| WO | 01/63001 A2 | 8/2001 |

* cited by examiner

BALLOON CATHETER AND METHOD OF MAKING SAME

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Balloons mounted on the distal ends of catheters are widely used in medical treatment. The balloon may be used to widen a vessel into which the catheter is inserted, force open a blocked vessel and/or deliver a medical device to a body location among other uses. The requirements for strength and size of the balloons vary widely depending on the balloon's intended use and the vessel size into which the catheter is inserted.

Applications such as balloon angioplasty require extremely thin walled high strength relatively inelastic balloons of predictable inflation properties. Thin walls are necessary because the balloon's wall and waist thicknesses limit the minimum diameter of the distal end of the catheter and therefore determine the limits on vessel size treatable by the method and the ease of passage of the catheter through the vascular system.

It is highly desirable for the balloon to be expandable more than once to a reproducible expanded position from an initial folded position. It is also desirable that on deflation the deflated balloon return to its initial configuration. Finally, it is desirable for the balloon and catheter to be easily maneuvered through the body lumen. These properties are determined in large measure by the cone section of the balloon as well as the flexibility of the catheter, and more particularly the catheter distal end region or tip.

There are a number of different approaches in the prior art to designing a balloon catheter having differing physical and mechanical properties in different sections of the catheter and/or balloon.

One such approach involves forming a balloon by stretching and blowing of the balloon from a segment of extruded polymer tubing. Balloons produced by stretching and blowing a tubular preform or "parison" typically have much thicker waist and cone walls than the wall thickness of their body portions. The thicker cone walls contribute to the overall thickness of the catheter, making tracking, crossing and re-crossing of lesions more difficult. Further, thick cones interfere with refolding of the balloon on deflation so that the deflated balloon can only be further inserted or withdrawn with difficulty, occasionally even damaging the blood vessel.

While there have been several solutions proposed for reducing the cone or waist thickness of catheter balloons in U.S. Pat. Nos. 4,906,241, 4,963,313, 5,304,340, 5,087,394, EP 318,919, EP 485,903, the procedures involved in these references are quite cumbersome.

Another approach involves the removal of material from the balloon cone, waist or other portion of the catheter balloon such as by chemically etching the balloon, laser ablating the balloon, etc. Such methods are described in U.S. Pat. No. 5,733,301 and U.S. application Ser. No. 09/781,388, filed Feb. 13, 2001, to Tomaschko et al. While methods of removing material are useful for a variety of reasons, they may not be particularly useful for encouraging balloon rewrapping and refolding, as well as catheter flexibility and trackability.

It is thus, a goal of the present invention to provide a balloon and/or a catheter device, and methods for producing same, that provide for various patterns and techniques for removing material from one or more regions of the catheter, including but not limited to the balloon cone, or other portion of the balloon, the catheter tip, and/or other regions of the catheter in order to encourage improved balloon refolding and rewrapping.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is embodied in a variety of forms. In at least one embodiment for example, the invention is directed to a balloon catheter having one or more cones and/or other regions of the balloon and/or catheter that define a pattern of one or more indentations such as grooves, notches, slits, etc., which extend to one or more predetermined depths into the thickness of the balloon wall. In at least one embodiment the depth of any given portion of the indentation pattern is not more than about half of the total thickness of the balloon wall.

In some embodiments, the pattern comprises one or more spiral, helical, or other shapes which extend about at least a portion of the balloon and/or catheter.

In some embodiments, at least a portion of the cone region of the balloon defines one or more indentations that extend into the wall of the balloon.

In some embodiments, at least a portion of the distal end region of the catheter defines one or more indentations that extend into the wall of the catheter shaft.

In some embodiments, at least a portion of the balloon wall is provided with one or more thinned out surfaces. In at least one embodiment, the external surface of at least one balloon cone is provided with a pattern of substantially flat surfaces, each surface intersects an adjacent surface along a hinge or fold line.

In some embodiments, at least a portion of the catheter shaft is provided with one or more thinned out surfaces.

In some embodiments, a balloon is provided with one or more indentations and/or substantially thinned out surfaces by laser ablating, chemically or mechanically etching or otherwise selectively removing material from one or more portions of the balloon.

In some embodiments, the distal end region of the catheter is provided with one or more indentations and/or substantially thinned out surfaces by laser ablating, chemically or mechanically etching or otherwise selectively removing material from one or more portions of the catheter.

In at least one embodiment a balloon catheter or portion thereof could be molded or otherwise formed with one or more indentations or substantially flattened or thinned surfaces therein.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
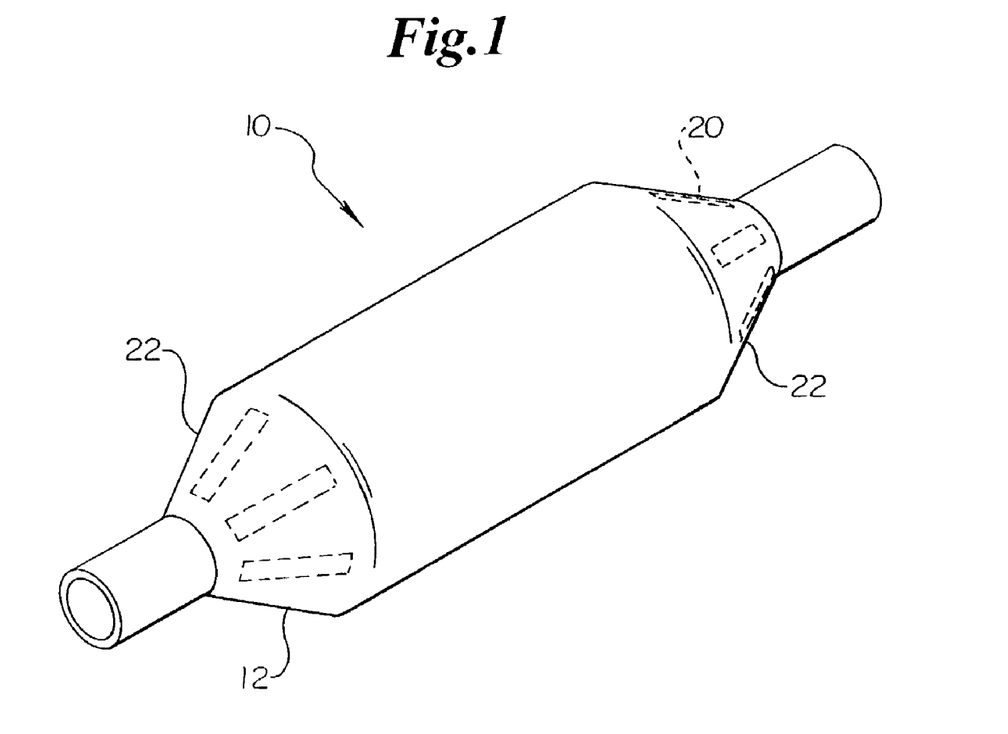
FIG. 1 is a perspective view of an embodiment of the invention wherein a balloon is show prior to selective removal of material from the cone portions.

As indicated above, the present invention comprises a variety of embodiments. For example, in the embodiment shown in FIG. 1, the invention is directed to a medical balloon, indicated generally at 10, having improved rewrapping and refolding characteristics. To provide the balloon 10 with such improved characteristics, one or more portions, such as are indicated by reference numeral 20, of the wall 12, of one or both cones regions 22, are removed, to a predetermined depth, by laser or heat ablation, chemical or physical etching or drilling, or by any other method desired.

Figure 2:
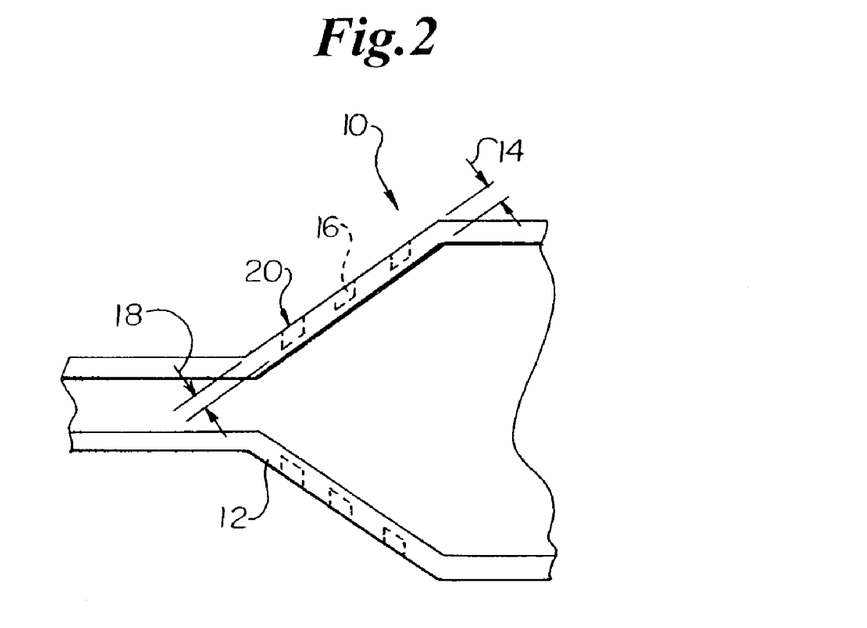
FIG. 2 is a partial cross-sectional side view of the embodiment shown in FIG. 1 wherein portions of material to be removed from the balloon cone are illustrated.

As is best shown in FIG. 2, the wall 12 has a predetermined thickness 14 which may be constant or varied along the length of the balloon 10. To maintain the integrity and functionality of the balloon 10 the portions 20 of the balloon material 16 which are to be removed from the wall 12 have a depth or height 18 which extends only partially through the thickness 14 of the wall 12.

For example, in some embodiments the thickness 14 of the wall 12 is between about 0.00025 inches to about 0.005 inches. In such an example, the desired depth 18 of the portion to be removed 20 may be about 0.00015 inches to about 0.004 inches.

Figure 3:
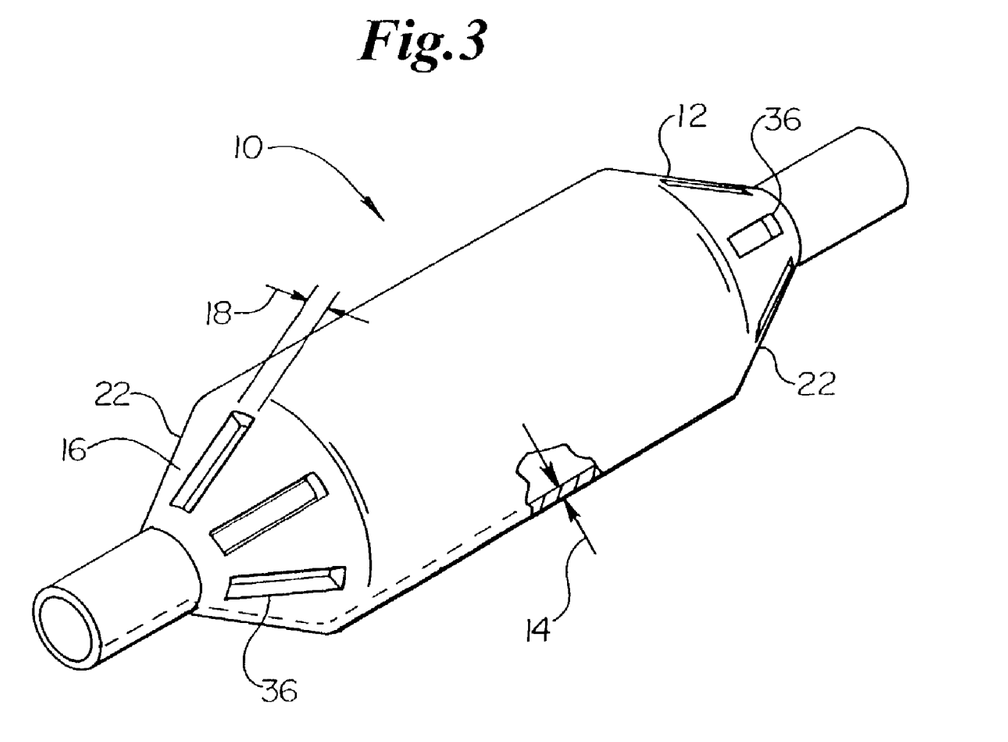
FIG. 3 is a perspective view of the embodiment shown in FIG. 1 after material has been removed from the balloon cones.
Figure 4:
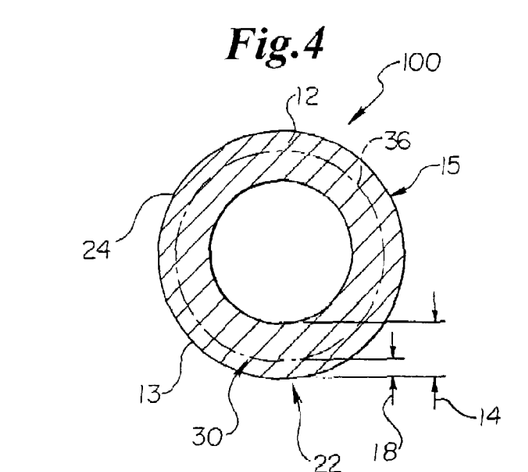
FIG. 4 is a cross-sectional view of an embodiment of the invention.

As is shown in FIG. 3, once the material is removed from the wall 12 by any method desired, the wall 12 will define one or more grooves, notches or indentations 36 which extend into the thickness 14 of the wall 12 to the depth 18 previously determined.

It must be noted that as an alternative, it is possible to form the wall 12 of the balloon 10 with the indentations 36 provided therein such as through the use of a mold or other device. Such a forming process may negate the need to ablate, etch or other wise remove material 16 as described.

In some embodiments such as are shown in FIG. 3, the wall 12 defines a plurality of individual indentations 36 that are scattered about at least a portion of the balloon 10, such as one or both of the cone regions 22, in a random or predetermined pattern 30. The individual indentations 36 may have the same or different depths as desired.

In some embodiments the portions of the catheter adjacent to the balloon, may also or alternatively be provided with one or more indentations such as are described herein.

In some embodiments, such as in the examples shown in FIGS. 4-9 a catheter, indicated generally at 100, comprises a tabular member or shaft 13 that defines one or more elongated indentations that form a continuous groove 36 through a portion of the shaft 13. The pattern that the groove 36 follows about the shaft exterior 25 may be any form. For example, in the embodiment shown in FIGS. 4-6 a single continuous groove 36 defines a spiral pattern 30 about at least a portion of the exterior 25 of shaft 13 adjacent to the balloon cone 22 of the balloon 10. In the embodiment shown in FIGS. 7-9 the groove 36 defines a crossing helix pattern 30. Other patterns may also be employed and are within the scope of this invention.

In the embodiments shown in FIGS. 4-9 the distal end region 15 of the catheter 100 is provided with one or more indentations or grooves 36. However it must be noted that any portion of the catheter 100 or balloon 10 may be provided with one or more indentations or grooves 36.

The pattern of the groove 36 applied to the catheter shaft 13 may be applied to any portion of the catheter 100 including but not limited to the balloon 10.

As is shown in the various embodiments, the depth 18 of the indentation(s) may be constant or varied as desired. For example in the embodiment shown in FIG. 3, the indentations may have the same or different depths relative to one another and/or relative to the thickness 14 of the balloon wall 12 or catheter shaft 13. In the embodiments shown in FIGS. 4 and 7 the depth 18 of the groove 36 relative to the thickness 14 of the shaft 13 along the length of the groove 36 may be constant or varied.

Figure 5:
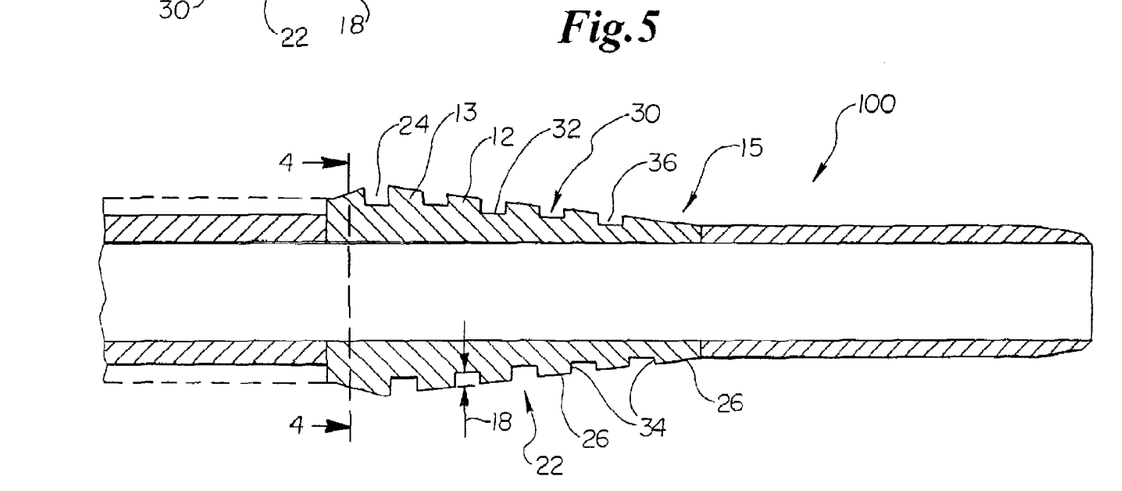
FIG. 5 is a cross-sectional side view of the embodiment shown in FIG. 4.
Figure 6:
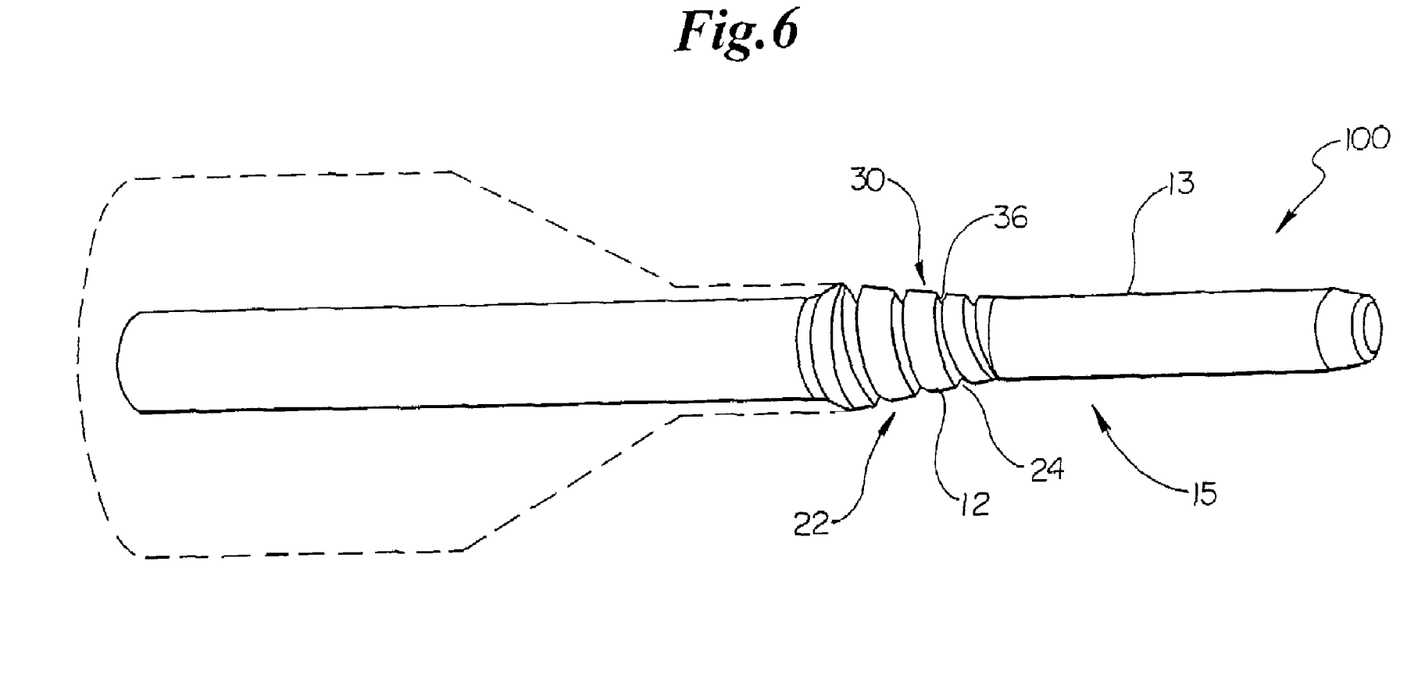
FIG. 6 is a perspective view of the embodiment shown in FIGS. 4 and 5.
Figures 7, 8:
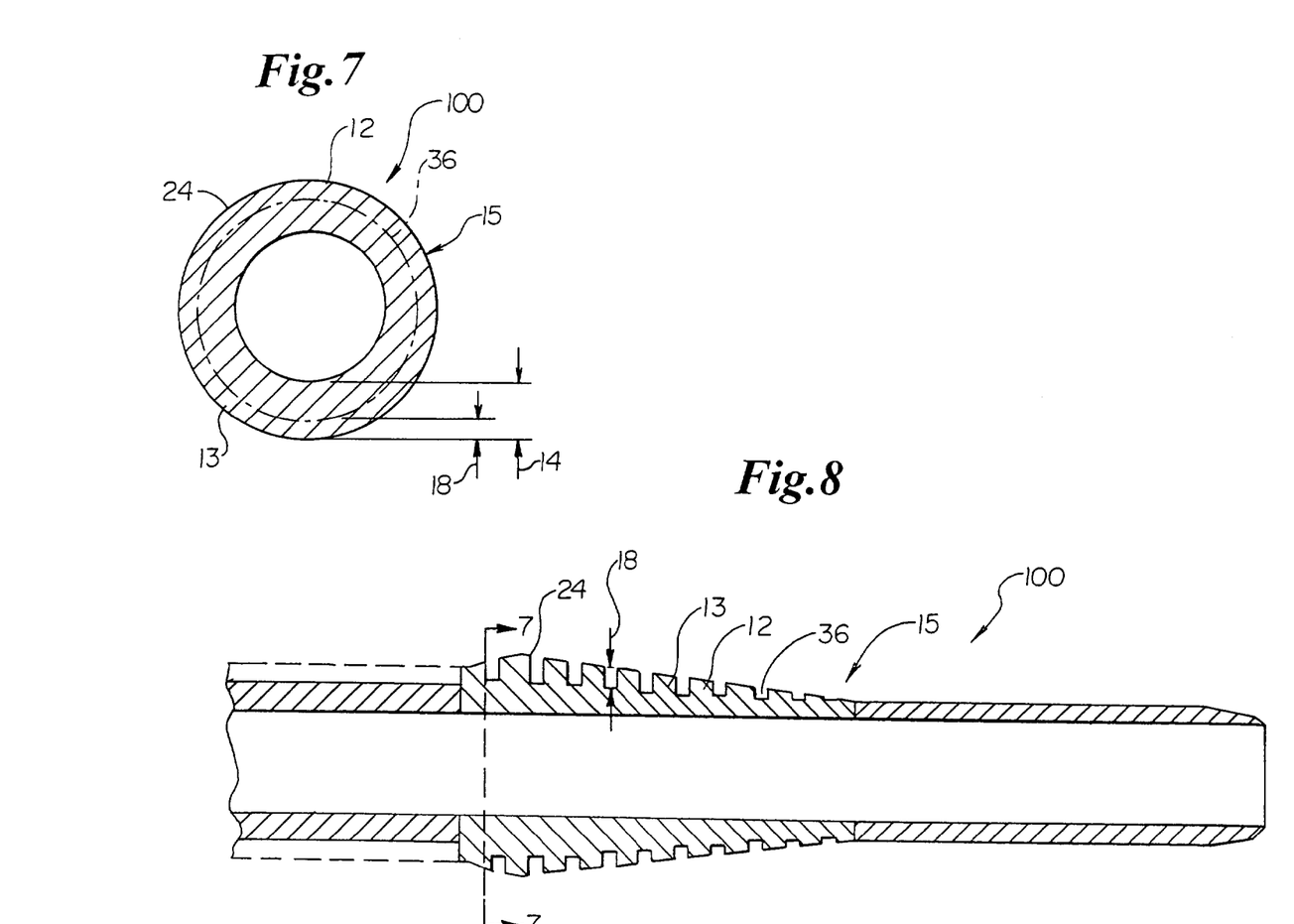
FIG. 7 is a cross-sectional view of an embodiment of the invention.
FIG. 8 is a cross-sectional side view of the embodiment shown in FIG. 7.
Figure 9:
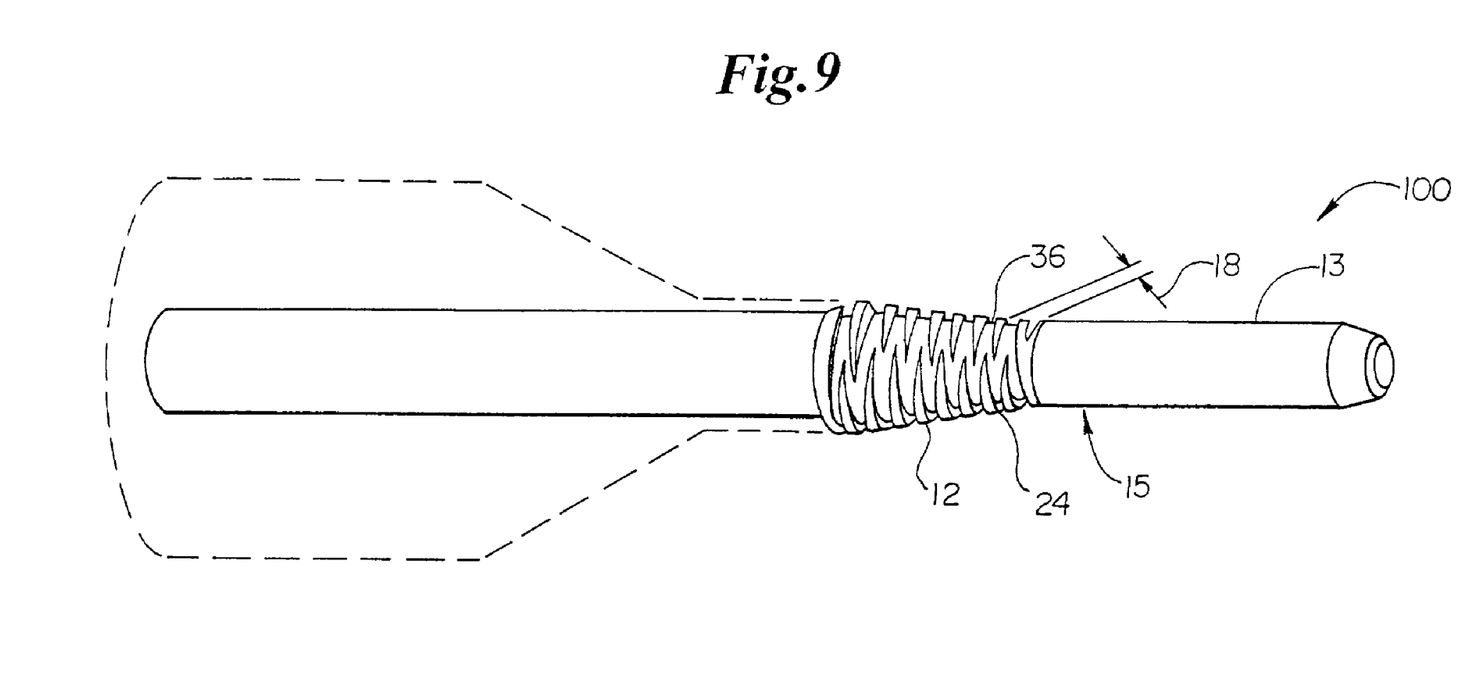
FIG. 9 is a perspective view of the embodiment shown in FIGS. 7 and 8.

As best depicted in FIG. 5, in the various embodiments shown, an indentation 36 will often be defined as a substantially U-shaped structure, V-shaped structure, or other shaped structure. A bottom surface 32 of the indentation is defined by the outside surface 24 of the balloon 10 and/or shaft 13. Sides 34 of an indentation 36 are defined by the surrounding portion 26 of the wall 12 and/or shaft 13. The indentations 36 define a space of about 0.1 mm to about 0.75 mm between sides 34.

In embodiments where multiple indentations 36 are spaced apart, or where portions of a single elongated indentation or groove 36 are spaced apart on the surface of the cone 22, the indentations or respective portions thereof are spaced 0.25 mm or more apart. In some embodiments, indentations, or portions thereof are spaced 0.5 mm or more apart.

Figures 10, 11, 12:
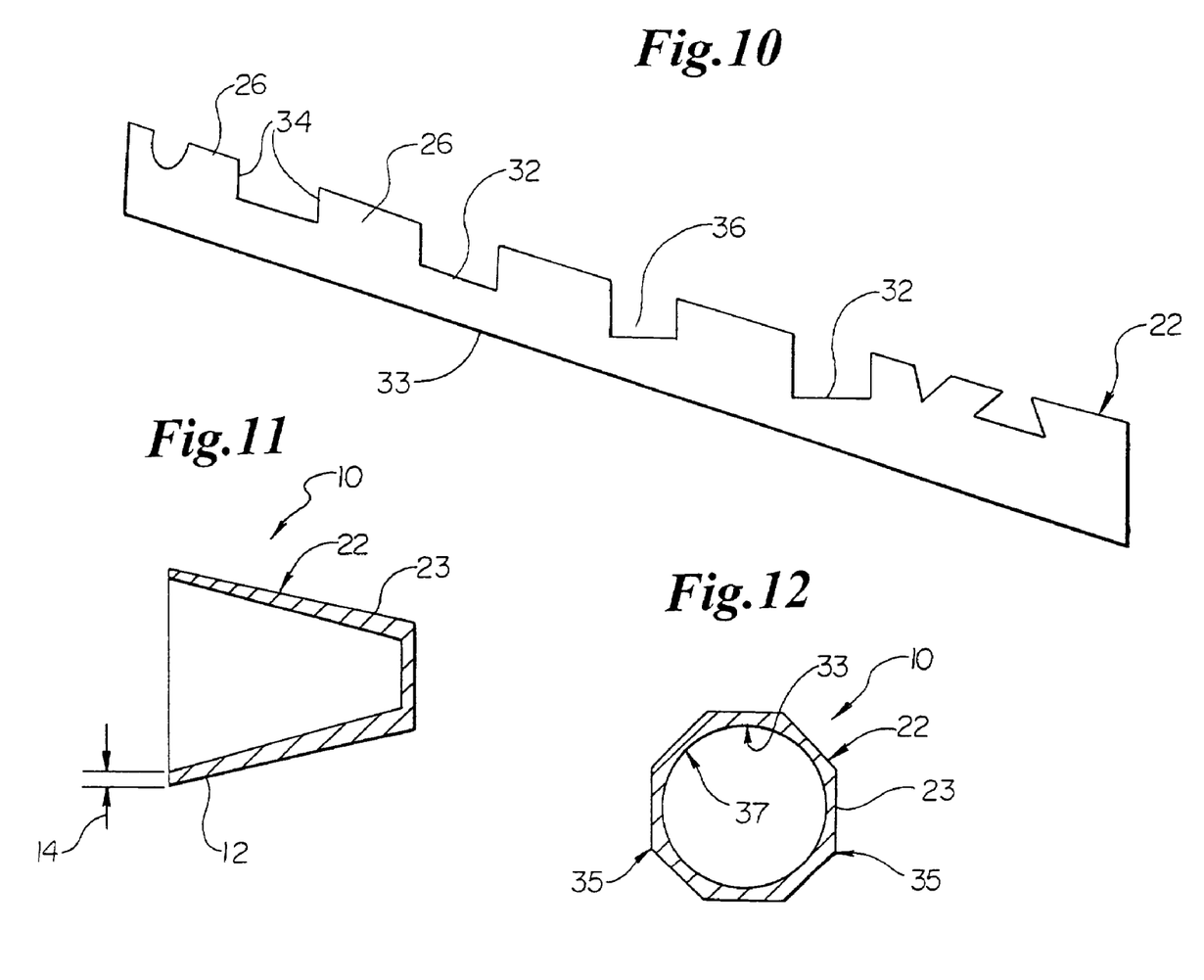
FIG. 10 is a close-up view of a portion of a balloon cone as processed in accordance with an embodiment of the invention.
FIG. 11 is a cross-sectional side view of an embodiment of the invention shown in the expanded state.
FIG. 12 is a cross-sectional view of the embodiment shown in FIG. 11.

In the various embodiments discussed thus far, one or more indentations 36 may be provided with a bottom surface 32 which is parallel to the interior surface 33 of the cone 22, such as is depicted in same of the grooves shown in FIG. 10. However, if desired the bottom 32 of one or more indentations 36 maybe non-parallel to the interior surface 33 of the cone 22 or angled in any manner desired. Similarly, the sides 34 of the indentations may or may not be parallel. The indentation or a portion thereof may be provided with any configuration desired including substantially converging sides, substantially diverging sides, substantially parallel sides etc. Where the catheter shaft 13 is provided with indentation, the bottom surface one or more indentation may be parallel or offset relative to the interior and/or exterior surface of the shaft.

Figure 13:
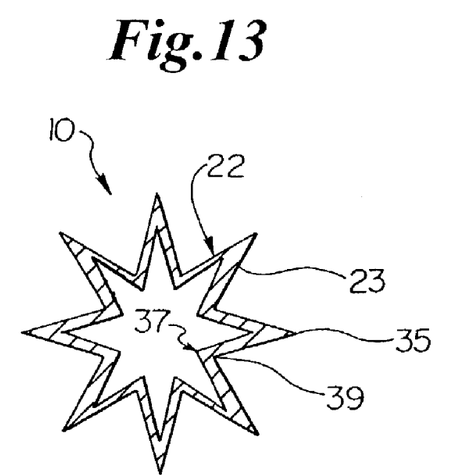
FIG. 13 is an cross-sectional view of the embodiment of the invention shown in FIGS. 12 and 13 wherein the balloon is shown in the unexpanded state.

Indenting or forming one or more indentations into the cones of a balloon or catheter shaft is but one mechanism for providing a balloon catheter with improved flexibility and for providing the balloon itself with improved folding and rewrap characteristics. Alternatively, in some embodiments, an example of which is shown in FIGS. 11-13, one or both of the cones 22 are provided with a plurality of distinct sides or substantially thinned out regions 23. Sides 23 may be formed by extruding the material of the balloon 10 through a form, molding the balloon in a mold having such the desired configuration of sides, cutting or etching a round member such as by mechanical grinding, chemical etching, laser ablation or other techniques.

The thickness of the balloon wall 12 where sides 23 are provided may be uniform or non-uniform as desired. In the embodiment shown in FIG. 12, for example, the substantially circular cross-sectional shape of the interior surface 33 of the balloon 10, helps to ensure that a middle portion 37 of each side 23 shape of the balloon has a reduced thickness relative to the adjacent portions of the side 23.

A balloon 10 may be provided with three or more sides 23. To this end, a balloon 10 may be provided with any of a wide variety of cross-sectional shapes when in the expanded state, such as for example: substantially triangular, substantially pentagonal, substantially hexagonal, substantially octagonal or any other shape or combination of shapes. For example, as is show in FIG. 12, a balloon 10 having eight sides 23 may be provided with a substantially octagonal shape when the balloon is in the expanded state.

Regardless of the number and shapes of sides 23 provided to a balloon 10, adjacent sides intersect at a first hinge point 35 about which adjacent sides 23 may fold inward when the balloon is in the unexpanded state, such as is shown in FIG. 13. In some embodiments, the sides 23 are equipped with a second hinge point 39 which allows the sides 23 to fold inward upon themselves during the balloon folding or rewrapping stage. In the embodiment shown in FIGS. 12 and 13, the second hinge point 39 corresponds to the portion of the sides 23 wherein the thickness of the wall 12 is narrowest, such as middle portion 37.

As hinge points 35 and 39, provide points about which adjacent areas of the cone 22 are able to fold, so to do the indentations 36 such as are shown in the embodiments depicted in FIGS. 1-10. The manner in which a balloon having indentations 36 may fold is depicted in FIGS. 14-16.

Figure 14:
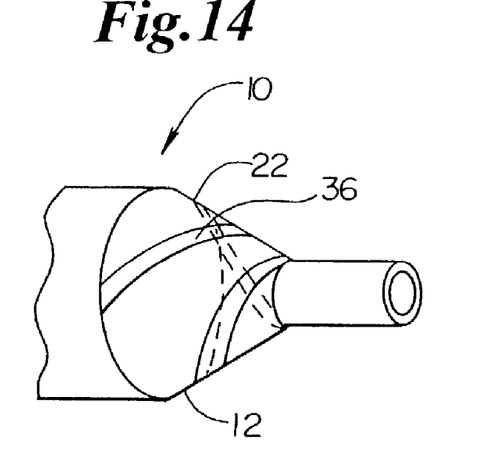
FIG. 14 is a perspective view of an embodiment of the invention shown in the expanded state.
Figure 15:
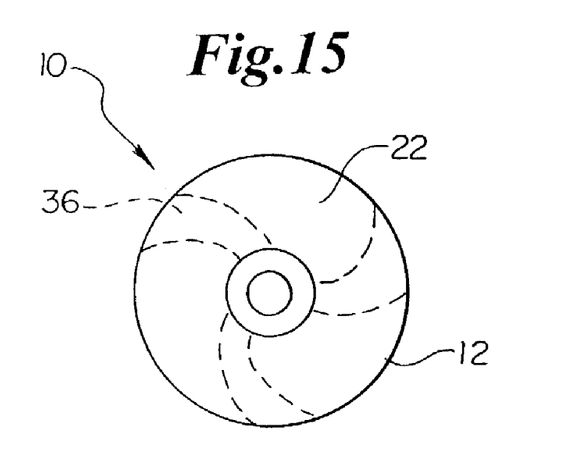
FIG. 15 is a cross-sectional view of the embodiment shown in FIG. 14.
Figure 16:
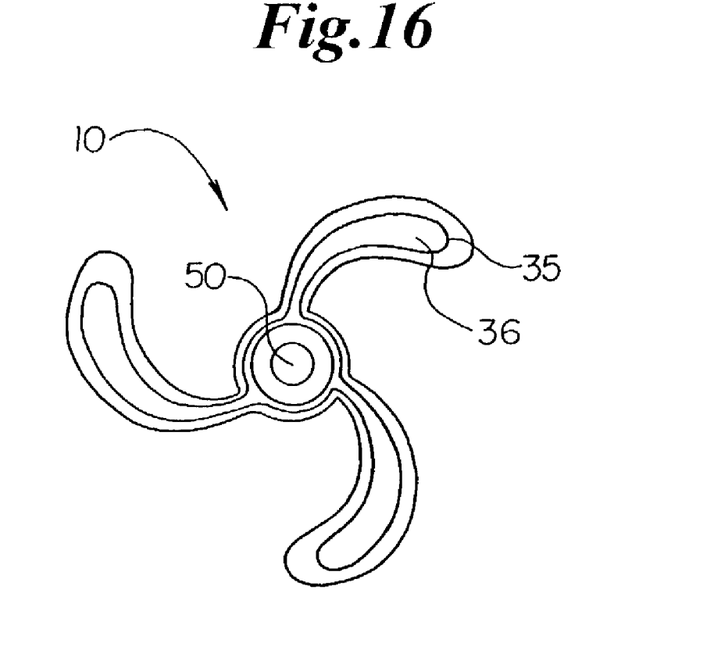
FIG. 16 is a cross-sectional view of the embodiment shown in FIGS. 14 and 15 wherein the balloon is shown in the unexpanded state.

In the embodiment show in FIGS. 14 and 15 a cone 22 of an expanded balloon 10 is shown having a plurality of indentations 36 in the wall 12 of the balloon. The indentations 36 are provided in a spiral like pattern. When the balloon 10 is placed in the unexpanded state as is shown in FIG. 16, the indentations 36 provide the balloon 10 with a plurality of hinge points 35 about which adjacent portions of the balloon can twist and fold inward toward the central axis 50 of the balloon 10.

As indicated above, other patterns of indentations may be provided to the cones of a balloon in order to provide the balloon with a variety of potential fold configurations.

Figure 17:
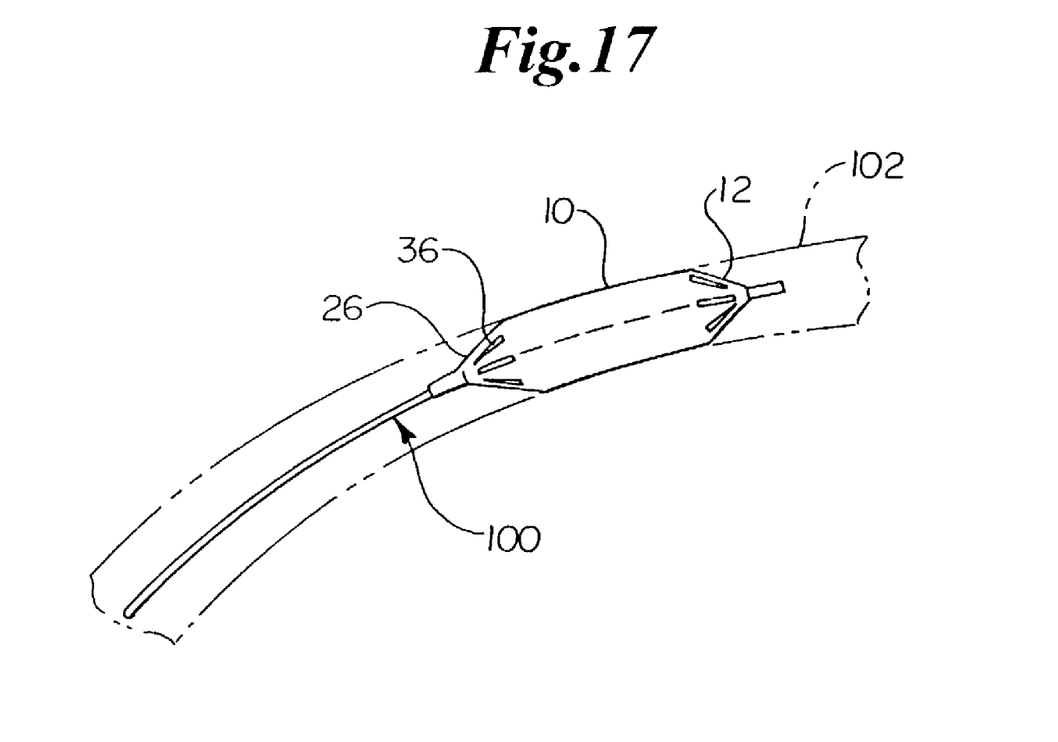
FIG. 17 is a cross-sectional side view of a vessel wherein an embodiment of the invention comprising a catheter equipped with a balloon is shown.

As may be seen in FIG. 17, a balloon 10, such as those having the features described above, may be incorporated into a catheter 100. The spaces 36 defined by the balloon wall 12 and/or the catheter shaft 13 provide the catheter 100 with improved flexibility as portions 26 of the balloon wall 12 and shaft 13 are able to utilize the spaces 36 to bend and flex around the various bends and curves of the vessel 102 where the balloon 10 may be positioned.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical balloon expandable between an expanded state and an unexpanded state, the balloon being defined by a wall, the wall having a thickness, an exterior surface and an interior surface, the balloon comprising a proximal cone portion, a distal cone portion, and a body portion therebetween, wherein the wall of at least one of the distal cone portion and proximal cone portion defines at least one indentation about which portions of the wall adjacent thereto fold inward when the balloon is in the unexpanded state, the at least one indentation comprising at least one circumferential groove extending about the wall of at least one of the distal cone portion and proximal cone portion in a substantially spiral-like pattern having a plurality of loops.

2. The medical balloon of claim 1 wherein the at least one indentation has a depth less than the thickness of the wall.

3. The medical balloon of claim 1 wherein the at least one indentation has a depth less than half the thickness of the wall.

4. The medical balloon of claim 1 wherein the depth of the at least one indentation is about 0.00015 inches to about 0.004 inches.

5. The medical balloon of claim 1 wherein the thickness of the wall is about 0.00025 inches to about 0.005 inches.

6. The medical balloon of claim 1 wherein each loop is separated by a distance of at least about 0.25 mm.

7. The medical balloon of claim 1 wherein each loop is separated by a distance of at least about 0.5 mm.

8. The medical balloon of claim 1 wherein the at least one circumferential groove defines at least two grooves, the at least two grooves each defining opposing helical patterns.

9. The medical balloon of claim 1 wherein the at least one indentation defines a plurality of indentations.

10. The medical balloon of claim 9 wherein adjacent indentations are separated by a distance of at least about 0.25 mm.

11. The medical balloon of claim 9 wherein adjacent indentations are separated by a distance of at least about 0.5 mm.

12. The medical balloon of claim 1 wherein the at least one indentation is formed by at least one technique selected from the group consisting of: laser ablation, mechanical grinding, drilling, chemical etching and any combination thereof.

13. The medical balloon of claim 1 wherein the wall of at least one of the distal cone portion and proximal cone portion defines a plurality of hinge points, the exterior surface of each portion of the wall adjacent thereto respectively define a substantially thinned out area, each of the substantially thinned out areas having at least one folding point, wherein in the unexpanded state portions of each substantially thinned out areas adjacent to the folding point fold inward when the balloon is in the unexpanded state.

14. The medical balloon of claim 13 wherein the exterior surface of the at least one distal cone portion and proximal cone portion has at least three substantially thinned out areas.

15. The medical balloon of claim 13 wherein the substantially thinned out areas of the exterior surface of the wall provide the at least one of the distal cone portion and proximal cone portion with a cross-sectional profile selected from at least one member of the group consisting of substantially triangular, substantially pentagonal, substantially hexagonal, substantially octagonal and any combination thereof.

16. The medical balloon of claim 13 wherein the substantially thinned out areas are formed by at least one technique selected from the group consisting of: laser ablation, mechanical grinding, drilling, chemical etching and any combination thereof.

17. A method of manufacturing a medical balloon having an expanded state and an unexpanded state, the balloon being defined by a wall, the wall having a thickness, an exterior surface and an interior surface, the balloon having a proximal cone portion, a distal cone portion, and a body portion therebetween, the method comprising the step of providing the wall of at least one of the distal cone portion and proximal cone portion with at least one indentation about which portions of the wall adjacent thereto are able to fold inward when the balloon is in the unexpanded state, the at least one indentation comprising at least one circumferential groove extending about the wall of at least one of the distal cone portion and proximal cone portion in a substantially spiral-like pattern having a plurality of loops.

18. The method of claim 17 wherein the at least one indentation is provided by selectively removing at least a portion of the at least one distal cone portion and proximal cone portion.

19. A catheter comprising:
a catheter shaft, a medical balloon being disposed about a portion of the catheter shaft, the medical balloon expandable between an expanded state and an unexpanded state, the medical balloon being defined by a wall, the wall having a thickness, an exterior surface and an interior surface, the medical balloon comprising a proximal cone portion, a distal cone portion, and a body portion therebetween, wherein the wall of at least one of the distal cone portion and proximal cone portion defines at east one indentation about which portions of the wall adjacent thereto fold inward when the balloon is in the unexpanded state, the at least one indentation comprising at least one circumferential groove extending about the wall of at least one of the distal cone portion and proximal cone portion in a substantially spiral-like pattern having a plurality of loops.

* * * * *